Figure 1:
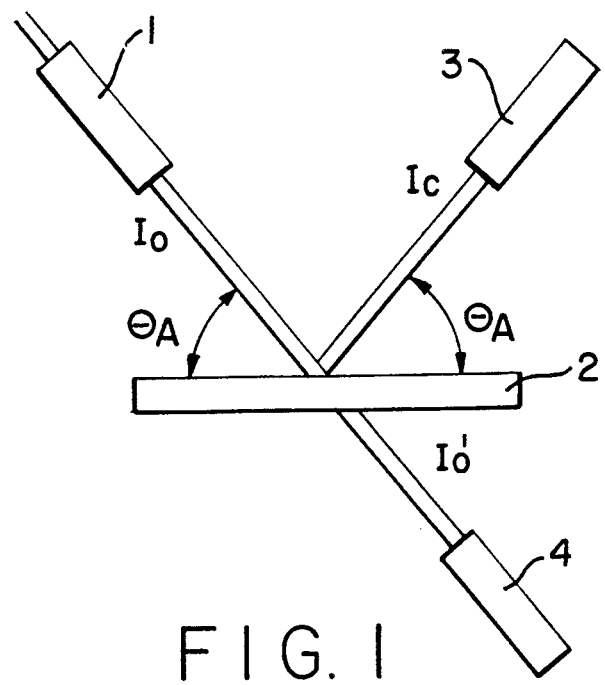

United States Patent [19]

von Ardenne et al.

[11] Patent Number: 5,057,688

[45] Date of Patent: Oct. 15, 1991

[54] METHOD FOR THE DETERMINATION OF THE ELEMENT CONCENTRATION IN ELECTRON BEAM MELTING

[75] Inventors: Alexander von Ardenne; Eckehard Madler; Bernd Wehner; Kurt Richter; Nicolas Schiller; Josef Tobisch, all of Dresden; Günter Hähnel, Freital, all of German Democratic Rep.

[73] Assignee: Bakish Materials Corporation, Englewood, N.J.

[21] Appl. No.: 576,015

[22] Filed: Aug. 31, 1990

[51] Int. Cl.⁵ .............................................. G01N 23/225
[52] U.S. Cl. .................................... 250/307; 250/310; 219/121.23; 378/46; 378/90
[58] Field of Search ............................... 250/307, 310; 219/121.23; 378/46, 90

[56] References Cited

U.S. PATENT DOCUMENTS 4,791,301 12/1988 Bauer et al. ............... 219/121.23
4,962,516 10/1990 Soezima ........................ 250/307

OTHER PUBLICATIONS

T. Kusamichi et al., "Fundamental Study on the Making of Titanium Alloy Ingot by Electron Beam Melting"; 10/29–31/89.
A. Mitchell et al., "Chemical Control in Electron Beam Melting"; 11/8–10/84.
A. Mitchell, "On-Line Composition Control in Vacuum Melting Systems"; 11/8–10/87.

Primary Examiner—Jack I. Berman
Attorney, Agent, or Firm—Nolte, Nolte and Hunter

[57] ABSTRACT

A method for determining the element concentration in electron beam melting is used for the continous measurement during the melting process especially for melting alloys. According to the invention, the X-radiation generated during melting is utilized by concurrently measuring the intensity of the characteristic radiation of the element to be determined and the intensity of another portion of the X-ray spectrum from the same location of the melt. The quotient of both measurands then is a function of the concentration of the element to be determined.

3 Claims, 1 Drawing Sheet

METHOD FOR THE DETERMINATION OF THE ELEMENT CONCENTRATION IN ELECTRON BEAM MELTING

OBJECT OF THE INVENTION

The invention relates to a method for the in-situ determination of the element concentration in electron beam melting in which the measurement can be carried out continuously during melting; a method to be used in the melting of alloys.

CHARACTERISTIC OF KNOWN ENGINEERING SOLUTIONS

In known techniques, samples are taken discontinuously so that the concentration has to be determined subsequently on the solidified and specially prepared sample. This method has the drawback that the measured results are available only after a relatively long time. Should a deviation from the dependent parameters occur, it is therefore impossible to act on the process in due time.

Moreover, it is known to employ an energy-dispersive spectrometer for the purpose. But this instrument can process a very restricted pulse rate only; a rate that is in the order of $10^4$ pulses per second. Because this pulse rate is distributed over the total spectrum, long measuring times are required to obtain the measuring accuracy required. Another disadvantage of the energy-dispersive spectrometer in the use of process control in metallurgy is the need to continuously cool the semiconductor with liquid nitrogen. As a consequence, there is no technique suitable for electron beam melting which allows for an in-situ routine determination of the element concentration at adequate precision within the short times required.

AIM OF THE INVENTION

The problem of the invention is to create a measuring technique for the determination of the element concentration which circumvents the deficiencies of the known measurement techniques, operates at a high precision with a rather low instrumental expenditure, and ensures easy handling.

DISCLOSURE OF THE INVENTION

This invention deals with the creation of a method for the continuous in-situ determination of the element concentration in electron beam melting. The steady and rapid change of the point of beam impingement on the melt, the very wavy bath surface, and the continuous or discontinuous lowering of the latter caused by the withdrawal of the ingot in the crystallizer shall not affect the measuring result. The time constant should be very small to allow for a rapid intervention in the melting process.

The problem is solved according to the invention in that the X-radiation occurring during electron beam melting is utilized so that the intensity of the characteristic radiation of the element to be determined is measured concurrently with the intensity of another portion of the X-ray spectrum from the same location of the melt, and that the quotient formed from both measurands represents a function of the concentration of the element to be determined.

It is of advantage to derive a ratio of the intensity of the characteristic X-radiation of the element to be determined to the intensity of a characteristic X-radiation of the basic element in the melt or to the intensity in a small wavelength range from the bremsspectrum.

Suitably, the characteristic X-radiation of the element to be determined can be measured by means of a crystal spectrometer.

There are various possibilities to measure the reference intensity. The intensity of a chosen range of the bremsspectrum should suitably be measured with the same crystal spectrometer used for the detection of the characteristic radiation of the element to be determined in which the higher orders of diffraction and the energy resolution of the detector are to be utilized. Another possibility to detect the reference intensity is to equip the crystal spectrometer with a thin analyzer crystal so that a portion of the primary spectrum penetrates the latter, and that a follow-up energy-resolving detector or a second crystal spectrometer can be used to measure the reference intensity.

EXAMPLE OF THE EMBODIED INVENTION

Figure 2:
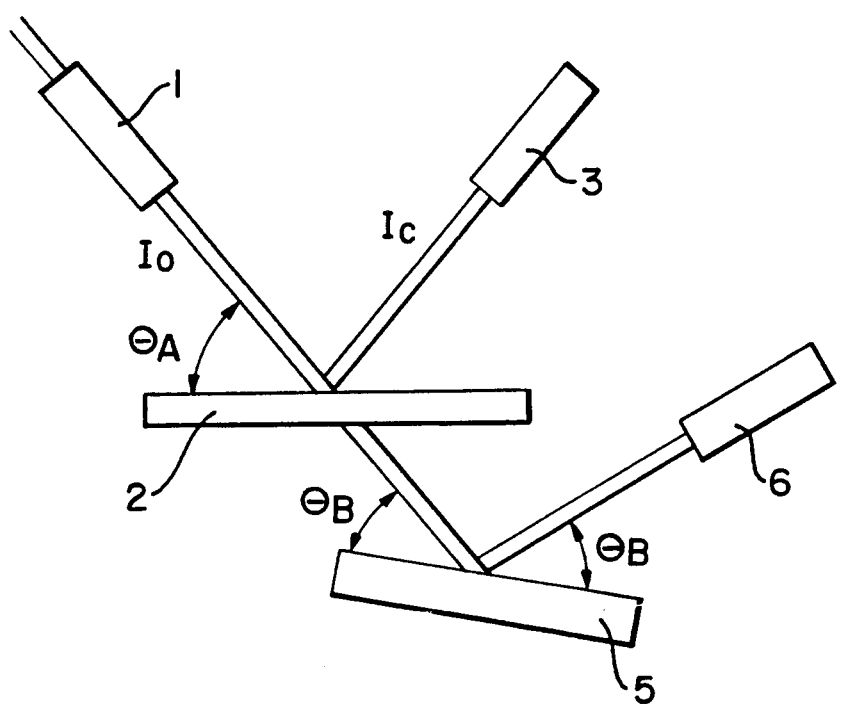

In the accompanying drawing
FIG. 1 is a schematic of the measuring setup with one analyzer crystal and
FIG. 2 is a measuring setup with two analyzer crystals.

The X-radiation is emitted in all spatial directions from a certain region of the melt that is cyclically passed or touched by the electron beam. Through a collimator 1 a portion of this radiation of the intensity $I_o$ approaches the analyzer crystal 2 as a so-called primary radiation (characteristic radiation and bremsstrahlung) under a defined angle $\theta_A$ that corresponds to the Bragg angle for a chosen characteristic radiation that is characterized by the wavelength $\lambda_C$. From the analyzer crystal 2 the said radiation is reflected under the like angle $\theta_A$. The detector 3 (e.g. a proportional counter tube) records the characteristic X-radiation $I_C(\lambda_C)$. The analyzer crystal 2 is so thin that the attenuated X-radiation $I_o'$ of the primary radiation $I_o$ penetrates the analyzer crystal 2 so that it can be recorded by detector 4 which is also a proportional counter tube.

With known means it is achieved that only a portion of the spectrum of the X-radiation $I_o$, i.e. $I_o'(\lambda_B)$, is evaluated for the acquisition of the monitor signal $S_M$. This monitor signal $S_M$ depends on the excitation energy of the electron beam in the same way as the useful signal $S_N$ which is derived from $I_C$. In that way, the quotient $S_N/S_M$ is rendered independent of the excitation energy. Moreover, other irregularities that affect the intensity of the X-radiation remain without influence on the quotient so that the latter solely depends on the element concentration.

The monitor signal $S_M$ may also be acquired by utilizing the characteristic X-radiation $I_C(\lambda_C/2)$ recorded by detector 3 that is reflected from the analyzer crystal 2 in the second order as a portion of the bremsspectrum. The pulses caused by $I_C(\lambda)$ and $I(\lambda/2)$ are separated by electronic means also. In this special variant the detector 4 can be dispensed with.

Another possiblility to acquire the monitor signal $S_M$ is illustrated in FIG. 2. The setup according to FIG. 1 is extended by another analyzer crystal 5 with its associated detector 6. Here the X-radiation $I_o'$ attenuated after penetration of the analyzer crystal 4 is spectrally dispersed by means of the analyzer crystal 5, and a portion of the bremsspectrum $I_B(\lambda_B)$ chosen in compliance with the Bragg angle $\theta_B$—which is either a portion of this spectrum or, in addition, contains the characteristic radiation of the basic element in the melt—is recorded and processed.

Suitably, the magnitude of the quotient $S_N/S_M$ should be optimized by arranging a foil or pinhole aperture in the beam path, preferably with the aid of selectively absorbing foils. Signal processing then takes place by means of known electronic means.

What is claimed is:

1. In a method for the determination of the element concentration in electron beam melting the utilization of the X-radiation generated thereby in which characteristic X-rays emitted from the elements contained in the melt are detected continuously and in situ by a detector via reflection from an analyzer crystal whereby the intensity of a portion of the X-ray spectrum obtained Via transmission through said analyzer crystal is also determined by a detector to form a ratio so that the said ratio of the two intensities is optimized as a function of the concentration of the element to be determined.

2. The method of claim 1 in which the ratio is formed from the intensity of the characteristic X-radiation of the element to be determined to that of the characteristic X-radiation from the basic element of the melt.

3. A method as set forth in the claims 1 or 2 in which the intensity of the portion chosen from the bremsspectrum and the characteristic radiation of the element to be determined are measured with the aid of only one detector and that the higher orders of diffraction are utilized for the purpose.

* * * * *